United States Patent
Lin et al.

(10) Patent No.: US 7,888,281 B2
(45) Date of Patent: Feb. 15, 2011

(54) SELECTIVE OXIDATION OF ALKANES AND/OR ALKENES TO VALUABLE OXYGENATES

(75) Inventors: Manhua Lin, Maple Glen, PA (US); Krishnan S. Pillai, North Brunwick, NJ (US)

(73) Assignee: Evernu Technology, LLC, Warminster, PA (US)

( * ) Notice: Subject to any disclaimer, the term of this patent is extended or adjusted under 35 U.S.C. 154(b) by 421 days.

(21) Appl. No.: 12/016,264

(22) Filed: Jan. 18, 2008

(65) Prior Publication Data

US 2008/0177106 A1 Jul. 24, 2008

Related U.S. Application Data

(60) Provisional application No. 60/885,767, filed on Jan. 19, 2007.

(51) Int. Cl.
*B01J 21/00* (2006.01)
*B01J 23/00* (2006.01)
*C07C 51/16* (2006.01)
*C07C 57/02* (2006.01)

(52) U.S. Cl. ............. 502/242; 502/249; 502/254; 502/304; 502/310; 502/314; 562/549; 562/598; 568/479

(58) Field of Classification Search ............ 502/311, 502/319, 242, 249, 254, 304, 310, 314; 562/549, 562/598; 568/479
See application file for complete search history.

(56) References Cited

U.S. PATENT DOCUMENTS

| | | | |
|---|---|---|---|
| 3,546,136 A | 12/1970 | Eden | |
| 4,260,822 A | 4/1981 | Krieger et al. | |
| 4,954,650 A | 9/1990 | Abe et al. | |
| 5,191,116 A | 3/1993 | Yamamatsu et al. | |
| 5,329,043 A | 7/1994 | Matsuura et al. | |
| 5,380,932 A | 1/1995 | Bielmeier et al. | |
| 5,380,933 A | 1/1995 | Ushikubo et al. | |
| 6,180,825 B1 | 1/2001 | Lin et al. | |
| 6,383,978 B1 * | 5/2002 | Bogan, Jr. | 502/311 |
| 6,403,525 B1 * | 6/2002 | Chaturvedi et al. | 502/311 |
| 6,407,280 B1 * | 6/2002 | Chaturvedi et al. | 558/319 |
| 6,514,901 B1 | 2/2003 | Lin et al. | |
| 6,514,903 B2 | 2/2003 | Lin et al. | |
| 6,589,907 B2 * | 7/2003 | Chaturvedi et al. | 502/311 |
| 6,812,366 B2 | 11/2004 | Lin | |
| 6,933,407 B2 | 8/2005 | Berndt et al. | |
| 7,012,157 B2 | 3/2006 | Borgmeier et al. | |
| 7,019,169 B2 | 3/2006 | Borgmeier et al. | |
| 7,026,502 B2 | 4/2006 | Benderly et al. | |
| 2005/0202964 A1 * | 9/2005 | Cavalcanti et al. | 502/311 |

FOREIGN PATENT DOCUMENTS

| | | |
|---|---|---|
| EP | 0418657 | 3/1991 |
| EP | 0495504 | 7/1992 |
| JP | 09278680 | 10/1997 |
| JP | 10128112 | 5/1998 |

OTHER PUBLICATIONS

K. Nagai, "New developments in the production of methyl methacrylate", Applied Catalysis A: General, 221: 367-377 (2001).
F. Cavani et al., "Main aspects of the selective oxidation of isobutane to methacrylic acid catalyzed by Keggin-type polyoxometalates", Catalysis Today, 71: 97-110 (2001).

* cited by examiner

*Primary Examiner*—Taylor Victor Oh
(74) *Attorney, Agent, or Firm*—Patrick J. Hagan; Dann, Dorfman, Herrell and Skillman, P.C.

(57) ABSTRACT

A catalyst, its method of preparation and its use for producing at least one of methacrolein and methacrylic acid, for example, by subjecting isobutane or isobutylene or a mixture thereof to a vapor phase catalytic oxidation in the presence of air or oxygen. In the case where isobutane alone is subjected to a vapor phase catalytic oxidation in the presence of air or oxygen, the product is at least one of isobutylene, methacrolein and methacrylic acid. The catalyst comprises a compound having the formula $$A_aB_bX_xY_yZ_zO_o$$

wherein A is one or more elements selected from the group of Mo, W and Zr, B is one or more elements selected from the group of Bi, Sb, Se, and Te, X is one or more elements selected from the group of Al, Bi, Ca, Ce, Co, Fe, Ga, Mg, Ni, Nb, Sn, W and Zn, Y is one or more elements selected from the group of Ag, Au, B, Cr, Cs, Cu, K, La, Li, Mg, Mn, Na, Nb, Ni, P, Pb, Rb, Re, Ru, Sn, Te, Ti, V and Zr, and Z is one or more element from the X or Y groups or from the following: As, Ba, Pd, Pt, Sr, or mixtures thereof, and wherein a=1, 0.05<b<1.5, 0.01<x<1, 0<y<0.5, 0<z<0.2 and o is dependent on the oxidation state of the other elements.

33 Claims, No Drawings

SELECTIVE OXIDATION OF ALKANES AND/OR ALKENES TO VALUABLE OXYGENATES

CROSS-REFERENCE TO RELATED APPLICATIONS

The present application claims the benefit of U.S. Provisional Patent Application No. 60/885,767, filed Jan. 19, 2007, the entire disclosure of which is incorporated by reference herein.

STATEMENT REGARDING FEDERAL SPONSORED RESEARCH OR DEVELOPMENT

The present invention was made with funds provided by the United State Department of Energy under Grant No. DE-FG02-02ER83420. The U.S. Government has certain rights in this invention.

FIELD OF THE INVENTION

The present invention relates to a catalytic process for preparing unsaturated oxygenates by subjecting an alkane or an alkene, or a mixture of alkane and alkene, having a carbon number from 2 to 6, to vapor phase oxidation in the presence of at least one catalyst and using air or oxygen as the oxidant. The alkane or alkene can be of straight chain or branched structures. The resulting oxygenates can be unsaturated C2 to C6 carboxylic acids, aldehydes, or a mixture thereof. The present invention further relates to a process for preparing a catalyst or catalysts useful for the above-mentioned catalytic process for preparing unsaturated oxygenates, and to the catalyst(s), per se.

In particular, the present invention relates to a catalytic oxidation process, using air or oxygen as the oxidant, which effectively and efficiently converts isobutane and/or isobutylene to the corresponding unsaturated aldehydes and/or carboxylic acids, i.e., methacrolein and/or methacrylic acid. In the case where alkane, or in particular isobutane alone is subjected to the catalytic oxidation process of the present invention, alkene, or in particular isobutylene can also be produced together with other oxygenates in the same catalytic oxidation process.

DESCRIPTION OF THE RELATED ART

Unsaturated aldehydes and carboxylic acids, such as acrolein, arylic acid, methacrolein and methacrylic acid, are important chemical building blocks that are suitable for use as monomers to be polymerized alone or with other monomers to produce commercially important polymer products. These unsaturated aldehydes and acids also serve as starting materials for the production of the corresponding esters, such as alkyl acrylate and alkyl methacrylate, which are useful for the preparation of a broad range of polymer products, such as plastic sheets and parts, paints and other coatings, adhesives, caulks, sealants, plastic additives, detergents, and the like.

Specifically with respect to the manufacturing of methacrylic acid or methyl methacrylate, the current commercial process involves a three-step reaction, commonly known as the ACH process, which was developed and commercialized in the 1930s. Currently, the ACH process is still the most commonly used process worldwide for the industrial production of methacrylic acid and/or its derivative, methyl methacrylate. The first step of the ACH process uses acetone and hydrogen cyanide as the starting materials. The second step of the ACH process uses an excess amount of concentrated sulfuric acid as the catalyst and solvent. The third step is a hydrolysis step leading to methacrylic acid, or an esterification step with methanol leading to methyl methacrylate. The main drawbacks of this ACH process are its utilization of the expensive and toxic starting material, HCN, the need for the usage and recycling of a large quantity of corrosive sulfuric acid, and its generation of large quantities of ammonium bisulfate and other toxic wastes.

Since the 1980s, several alternative processes using different starting materials have been explored in an attempt to replace the ACH process (See, for example, F. Cavani et al. *Catalysis Today*, 71 (2001) 97-110 and K. Nagai *Applied Catalysis A: General* 221 (2001) 367-377). Most of these alternative processes are still under development. However, a process using isobutylene as the starting material has been developed and commercialized in Japan since the 1980s.

The process utilizing isobutylene or t-butanol as the starting material is a two-step process. As described in U.S. Pat. No. 4,954,650 to Abe et al., isobutylene or t-butanol is oxidized to methacrolein over catalyst-1, for example, in reactor-1, and the resulting methacrolein is further oxidized to methacrylic acid in reactor-2 over catalyst-2. Nearly complete conversion of isobutylene, with an overall one-pass methacrylic acid yield up to 69%, has been reported for this process. However, this two-step isobutylene-process does not appear to be attractive to most manufactures, since the ACH process is still the dominant industrial process worldwide for producing methacrylic acid or methyl methacrylate.

Alternatively, the production of methacrylic acid or methyl methacrylate can proceed through a one-step catalytic oxidation of isobutane in the gas phase. Such a process is especially desirable and advantageous as compared to both the three-step ACH process and the two-step isobutylene or t-butanol process mentioned above, because the cost of alkanes in general, and isobutane in particular, is significantly less than other starting materials, such as acetone and HCN for the ACH process, or the isobutylene for the commercial isobutylene process.

A commercially viable process for the manufacture of unsaturated aldehyde/acid through the catalytic oxidation of an alkane requires the development of a catalyst achieving an adequate conversion of the alkane, and a suitable selectivity to the desirable unsaturated aldehyde or acid, thereby providing a sufficient yield of the oxygenate products. Another requirement essential for commercialization is a suitable stability and durability of the catalyst under the conditions employed in the reaction. However, none of the prior art processes using isobutane as the starting material appear to provide any viable catalysts which have the potential to meet the commercial requirements of activity, selectivity and durability.

U.S. Pat. No. 4,260,822 to Krieger et al. discloses a one-step process for the production of methacrylic acid from isobutane. The catalyst disclosed therein is a heteropoly compound (HPC) consisting of P, Mo, and Sb, which achieved 10% isobutane conversion and 5% yield of methacrylic acid and 2% yield of methacrolein, respectively. Similarly, European Patent No. 418,657 A3, European Patent No. 495,504 A2, U.S. Pat. No. 5,191,116 to Yamamatsu et al. and U.S. Pat. No. 5,380,932 to Bielmeier et al. disclose that HPC catalysts containing P, Mo, V can also achieve about 70% of combined selectivity to methacrylic acid and methacrolein with about 10% isobutane conversion. However, any potential for increased productivity using these catalysts is inherently limited, since they exhibit linear decreases in selectivity as the isobutane conversion increases at higher temperature (See discussions in K. Nagai, supra). In addition to the low productivity issue, a short catalyst life under the required high temperature reaction conditions has also been identified as one of the shortcomings of these HPC catalysts.

U.S. Pat. No. 5,329,043 to Matsuura et al., on the other hand, discloses a catalyst containing divanadyl pyrophosphate with a general formula of P—V—XYZ which is reported to achieve somewhat improved isobutane conversion, but with slightly less combined selectivity to methacrylic acid and methacrolein, as compared to the heteropoly compound catalysts.

U.S. Pat. No. 5,380,933 to Ushikubo et al. (the '933 patent) discloses the preparation of a mixed metal oxide catalyst, containing Mo, V, Te, and Nb and exhibiting a set of five characteristic X-ray diffraction peaks at 22.1°, 28.2°, 36.2°, 45.2° and 50.0° 2θ, which was found to be highly effective for the production of acrylic acid via the catalytic oxidation of propane (C3 alkane). The '933 patent also alludes to the effectiveness of such catalyst for the selective oxidation of C4 alkanes, i.e. isobutane and n-butane, in producing unsaturated oxygenates. However, the oxidation of n-butane (a C4 alkane) produced no C4 oxygenates, but rather acrylic acid (C3) as the only unsaturated oxygenate reported, with selectivity of less than 20% (Examples 9 and 10 of '933 patent). The '933 patent describes no actual example of the oxidation of isobutane, nor does it report or suggest any unsaturated acids, other than acrylic acid, as the products to be expected from the process disclosed therein.

Furthermore, U.S. Pat. Nos. 6,180,825, 6,514,901 and 6,514,903, all to Lin et al., disclose an improved process for the preparation of the same Mo—V—Te—Nb mixed metal oxide catalyst having the same set of X-ray diffraction peaks as disclosed in the '933 patent. U.S. Pat. No. 6,812,366 to Lin discloses the use of the same Mo—V—Te—Nb catalyst, having the same characteristic set of X-ray diffraction patterns as specified by the '933 patent, for the production of acrylic acid from propane, propene and other C3 oxygenates. U.S. Pat. Nos. 7,012,157 and 7,019,169, both to Borgmeier et al., also disclose improved processes for the preparation and utilization of mixed metal oxides containing Mo—V—Te—Nb, as disclosed in the '933 patent. The catalysts thus prepared according to these improved methods have been shown to be effective for the production of acrylic acid from propane. However, none of the patents mentioned immediately above include any description of actual examples of catalytic oxidation of C4 alkanes (i.e., n-butane or isobutane) over the claimed mixed metal oxide catalysts, nor was there any reported formation of any C4 oxygenates. This is not surprising, since the inventions disclosed in these patents mentioned immediately above are not concerned with any new catalyst, but with different methods of making the same Mo—V—Te—Nb catalyst disclosed by the original '933 patent.

The actual catalytic oxidation of isobutane over Mo—V—Te—Nb mixed metal oxide catalysts, such as disclosed in the '933 patent and other related patents, as well as Mo—V—Sb—Nb catalysts, leading to C4 oxygenates is disclosed in Japanese Laid-Open Patent Applications No. 09-278,680 and 10-128,112, both to Okusako et al. The isobutane conversion disclosed therein was in the range of 5-6%, while the combined yield of methacrylic acid and methacrolein was only in the range of 1-1.8%, which is significantly lower than that achievable by the above-mentioned HPC catalysts, and clearly inadequate for commercialization.

Alternatively, U.S. Pat. No. 6,933,407 to Berndt et al. discloses the production of methacrylic acid via a three-step process starting from isobutane over three different catalysts in three different reactors. The first reactor is a dehydrogenation reactor using catalyst containing metals, including Pt. In the dehydrogenation reactor, isobutane is converted to isobutylene and gaseous $H_2$, which is removed before the product mixture of isobutylene and unreacted isobutane is fed to the second reactor. In the second reactor, isobutylene is converted to methacrolein over a catalyst containing metal oxides while isobutane remains. Product methacrolein is then separated from the unreacted isobutane and fed to the third reactor, where it is converted to methacrylic acid over a third catalyst containing metal oxides, which differs from the second metal oxide catalyst. Overall, the one-pass conversion of isobutane was reported to be around 25% and one-pass overall yield of methacrylic acid was around 9%.

In summary, the state of the art of processes for the production of methacrylic acid or methacrolein through a one-step isobutane catalytic oxidation is rather undeveloped. (See K. Nagai, supra). Most disclosed catalysts of the heteropoly compound-type offer undesirably low isobutane conversions, as well as short catalyst-lives. On the other hand, the mixed metal oxide catalysts of the Mo—V—Te—Nb and Mo—V—Sb—Nb-types, such as those which are the subject of U.S. Pat. No. 5,380,933, while effective for producing acrylic acid from propane, were specifically found to be ineffective for producing methacrolein or methacrylic acid from isobutane. The alternative process disclosed in U.S. Pat. No. 6,933,407, requires not only multiple reactors, including a dehydrogenation reactor, but also entails complicated procedures for product separation after each step.

SUMMARY OF THE INVENTION

According to one aspect of the present invention, there is provided a solid, metal oxide catalyst comprising a compound having the formula

$A_a B_b X_x Y_y Z_z O_o$ wherein A is at least one of the group of elements Mo, W and Zr, B is at least one of the group of elements Bi, Sb, Se and Te, X is at least one of the group of elements Al, Bi, Ca, Ce, Co, Fe, Ga, Mg, Ni, Nb, Sn, W and Zn, Y, if present, is at least one of the group of elements Ag, Au, B, Cr, Cs, Cu, K, La, Li, Mg, Mn, Na, Nb, Ni, P, Pb, Rb, Re, Ru, Sn, Te, Ti, V and Zr, and Z, if present, is at least one element from said X or Y groups or from the following: As, Ba, Pd, Pt, Sr, or mixtures thereof, and wherein a=1, 0.05<b<1.5, 0.01<x<1, 0<y<0.5, 0<z<0.2 and o is dependent on the oxidation state of the other elements.

In another aspect, the present invention provides a process for preparing the above-described catalyst, which comprises the following steps:

a) forming a mixture comprising appropriate amounts of source materials containing selected ones of the aforementioned elements to provide such elements in predetermined a, b, x, y and z ratios and, optionally, at least one liquid substance in an amount sufficient to provide a solution or slurry of the source materials;

b) removing from said mixture part or all of the liquid substance(s), if present, to obtain a solid catalyst precursor; and c) calcining the catalyst precursor at a temperature from 150° C. to 900° C. under an atmosphere containing oxygen, or an inert gas or a mixture thereof, to yield the solid catalyst.

According to still another aspect, the present invention provides a process of using the above-described catalyst for the production of unsaturated aldehyde and/or unsaturated carboxylic acid from an alkane and/or alkene of the same or less carbon number. This method comprises subjecting a feed gas mixture including an alkane, an alkene, or a mixture thereof, and air or oxygen, and one or more inert diluting gases, when needed, to a vapor phase oxidation in a heated reactor in the presence of a catalyst having the composition described herein. In the case where an alkane alone is subjected to the vapor phase catalytic oxidation described herein, the product is at least one or more of alkene, unsaturated aldehyde, and unsaturated acid of the same or less carbon number.

DETAILED DESCRIPTION OF THE INVENTION

The present invention concerns a complex metal oxide catalyst, its method of preparation and its use for the production of unsaturated aldehydes and/or unsaturated carboxylic acids, such as methacrolein and/or methacrylic acid, by subjecting an appropriate alkane and/or alkene, such as isobutane or isobutylene or a mixture thereof, to gas phase oxidation in the presence of air or oxygen under certain oxidation conditions over a metal oxide catalyst of certain specific composition, which may be a bulk solid substance or a substance dispersed onto and/or into a support material of high surface area. The present invention can be applied to various C2-C6 alkanes and/or alkenes for the production of the corresponding oxygenates of the same carbon number. However, alkenes and/or other oxygenates with the same or lesser carbon atoms than the original alkane or alkene may also be present as part of the oxidation products. For instance, when isobutane alone is subjected to the vapor-phase catalytic oxidation of this invention, the product is at least one or more of isobutylene, methacrolein and methacrylic acid, respectively. Furthermore, to enhance the production economics or the utilization of starting materials, the unreacted alkane and alkene and/or the alkene in the product stream (after the unsaturated carboxylic acids and aldehyde are separated therefrom, either separately or together as a mixture) may be recycled and mixed with fresh alkane and/or alkene to form the feed mixture.

In carrying out the method of the invention, suitable alkanes and/or alkenes are caused to undergo gas-phase oxidation in the presence of a complex metal oxide catalyst having the basic formula

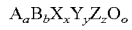

$A_aB_bX_xY_yZ_zO_o$ wherein A, B, X, Y, Z, O, a, b, x, y, z and o, are as previously defined.

In one embodiment, the catalyst of the invention has the above formula, wherein A is Mo or W or a mixture thereof, B is at least one of the group of elements Bi and Sb, X is at least one of the group of elements Bi, Ca, Ce, Co, Ga, Mg, Ni, Sn, and Zn, Y, if present, is at least one of the group of elements Ag, Au, La, Mn, P, Pb, Sn, Te, and Zr, and Z, if present, is at least one of the elements from the X group, Y group or Al, B, Ba, K, Na, Pd and Sr.

In another embodiment, the catalyst of the invention has the above formula, wherein A is Mo, B is Sb, X is at least one of the group of elements Bi and Ce, Y, if present, is at least one of the group of elements Ag, Au, and Sn, and Z, if present, is at least one element from the X group, Y group or Al, B, Ba, K, Na, Pd and Sr.

The chemical composition, and hence the resulting structure and catalytic property of the catalysts of this invention, is distinctively different from the prior art catalysts discussed above. Specifically, the catalysts of this invention are not heteropoly acids or salts and are compositionally different from Mo—V—Te—Nb—O and Mo—V—Sb—Nb types of metal oxide catalysts disclosed in the '933 and related patents, which were shown to be ineffective for producing methacrolein and/or methacrylic acid from isobutane. Mixed metal oxide catalysts with the general formula $A_aB_bX_xY_yZ_zO_o$ as described herein are specifically effective in producing methacrolein and/or methacrylic acid from isobutane and/or isobutylene.

The mixed metal oxide catalysts with the general formula $A_aB_bX_xY_yZ_zO_o$ can be prepared in the following manner.

The first step is the preparation of a catalyst precursor, which is a solid substance containing all of the essential metal elements, and which will lead to a mixed metal oxide catalyst after being subjected to calcination at elevated temperatures. The sources of each element used for the preparation of such a precursor can be selected from a wide range of materials, including oxides, halides, nitrates, alkoxides, oxalates, hydroxides, acetates, or various other organometallic compounds containing the element, or metal elements in the form of fine metal particles. The forms of these materials can be a liquid, a solution, a slurry or a solid. Thus, the mixing of source materials can involve the mixing of one or more individual liquids, solutions, slurries or solids. When all elements are introduced in solid forms, the resulting solid mixture can be further ground to enhance the thorough mixing of the elements. When one or more elements are introduced as a solution or a slurry, the liquid substances that are suitable for the preparation of the solution or slurry of a source material can be selected from water or various other organic liquids, such as alcohols, ketones, ethers, acids, and aliphatic or aromatic compounds. The solid catalyst precursor can be obtained after the partial or complete removal of the liquid substance(s) or solvent(s) from the mixture. The liquid substance(s) or solvent(s) can be removed using various methods, including air-drying, freeze-drying, spray drying, filtration, rotary evaporation, or evaporation under reduced pressure and/or various temperatures. Various other techniques known in the art, such as hydrothermal synthesis, sol-gel process, col-gel process, or various precipitation techniques can also be applied for the preparation of the catalyst precursor.

The catalyst precursor thus obtained is then calcined at suitable temperatures in proper stages for a suitable amount of time and under a suitable atmosphere for each stage to form the desired metal oxide catalyst. A suitable atmosphere can be different for each calcination stage, and may be inert, such as nitrogen or argon (the latter being more preferred), or oxidative, such as air, or reducing, such as hydrogen. The calcination temperature usually starts at close to room temperature and then is raised to a different temperature for each of the later stages ranging from about 150° C. to 900° C. The preferable temperature for the higher calcination stage is from 450° C. to 700° C. Likewise, the duration for each calcination stage can be different. Typically, the overall calcination is performed from 1 to 30 hours and preferably, the duration of the high temperature stage is from 2 to 10 hours, to obtain a desirable mixed metal oxide catalyst having the formula $A_aB_bX_xY_yZ_zO_o$ wherein A, B, X, Y, Z and a, b, x, y, z and o are as defined above. As previously noted, the molar ratio, o, i.e., the amount of oxygen (O) present in the finished catalyst is dependent on the oxidation state and the ratio of the other elements in the catalyst, i.e., A, B, X, Y and Z.

The mixed metal oxide, thus obtained as a bulk solid catalyst, exhibits excellent catalytic properties when used as is. However, improved catalytic performance can be attained by grinding the resulting metal oxide to fine particles. The mixed metal oxides thus obtained may also be incorporated, at different preparation stages, onto and/or into a high surface area support material, using various techniques well known in the art. Suitable support material include, without limitation, oxides, carbides, or nitrides of one or more element from the group of Al, Mg, Nb, Si, Ti, and Zr or composites thereof. The support material can be in the form of structure selected from particles, fibers, ceramic foam, monolith or fabric. The dispersion of the elements of the metal oxide catalyst onto and/or into the suitable support material can be accomplished by various techniques well known in the art, such as wetting, impregnation, sol-gel, co-gel, precipitating, co-precipitating, ion-exchange, vapor depositing, reverse micro-emulsion depositing or a combination thereof. Further, the resulting supported catalysts may be molded into a suitable shape and size depending on the size and shape of the reactor to be used.

Another aspect of the present invention comprises introducing alkanes or alkenes, or a mixture thereof, in the gas phase into a reactor containing the above described mixed metal oxide, in the presence of air or oxygen and diluting gas(es), when needed, to produce the desired unsaturated aldehyde, unsaturated carboxylic acid or mixture thereof. In the case where an alkane alone is subjected to the vapor phase catalytic oxidation of this invention, the product is at least one of alkene, unsaturated aldehyde, and unsaturated acid of the same or less carbon number. Suitable amounts of water vapor or steam can be incorporated into the feed-gas mixture, which may function as a diluting gas and enhance the selective formation of the desirable oxygenates. Furthermore, inert gas such as nitrogen, argon or helium or a pseudo-inert gas such as carbon dioxide or the like may also be incorporated into the feed gas mixture as diluting gases, if desired. In the case of the production of methacrolein or methacrylic acid or a mixture thereof, the feed-gas to the reaction system is a mixture in the appropriate ratios of A) fresh isobutane or isobutylene or a mixture thereof; B) oxygen or air, C) inert diluting gas(es), such as nitrogen or argon or helium or carbon dioxide, D) steam, and E) in the case of recycling, un-reacted isobutane and/or isobutylene from the feed and/or product isobutylene from isobutane exist in the reactor outlet stream. The molar ratio of hydrocarbon/(oxygen or air)/inert dilute gas/steam (A+E):B:C:D of the feed-gas mixture can be (1):(0.1 to 20):(0 to 20):(0 to 70). Also, care should be taken to assure that the hydrocarbon to oxygen ratio in the feed-gas, as well as in the reaction zone and the outlet, is maintained outside the flammable region for such a mixture. When isobutane alone is subjected to a vapor phase catalytic oxidation in the presence of air or oxygen, the product is at least one of isobutylene, methacrolein and methacrylic acid.

While the detailed mechanism of the catalytic oxidation reaction of the present invention is not yet fully elucidated, it is believed that the oxidation reaction is sustained by the molecular oxygen present in the feed gas (either from air or oxygen). However, gas phase oxidation of isobutane, isobutylene or a mixture thereof is also possible in the absence of molecular oxygen. In such a case, the lattice oxygen atoms in the metal oxide catalysts are consumed during the oxidation of hydrocarbons while the catalysts are reduced accordingly. As such, the enhanced selectivity to the desired unsaturated aldehydes and/or unsaturated carboxylic acids may be obtained in the absence of molecular oxygen in the gas phase. In that case, however, a separate step for the regeneration of the catalyst would be required. The reduced metal oxide catalysts can be regenerated by being exposed to an atmosphere containing molecular oxygen or other oxygen sources under suitable conditions.

The above mentioned oxidation of isobutane and/or isobutylene can take place utilizing a fixed bed system or a fluidized bed system. This reaction can be conducted at atmospheric pressure or under an elevated pressure. A suitable reaction temperature is from 200° C. to 600° C., but is preferably from 300° to 550° C. The feed-gas flows at a space velocity (SV) range of 360 to 36,000 hr-1, with the corresponding feed-gas and catalyst contact time being in the range of 10 to 0.1 seconds.

When isobutane is subjected to catalytic oxidation according to the present invention, methacrolein and methacrylic acid are the desired products. However, as stated above, other oxidation and partial oxidation products, such as carbon oxides, acetic acid, acetone, acrylic acid and isobutylene may also be produced as by-products. Among these by-products, isobutylene is also an oxidation intermediate which can be further oxidized to methacrolein or methacrylic acid. It is, therefore, beneficial to separate isobutylene as well as the unreacted isobutane from the other components of the reactor outlet stream and recycle them for incorporation into the in-coming feed-gas mixture. It is a common practice in the chemical industry to recycle unreacted starting materials and/or intermediates to increase efficiency and productivity and to avoid the waste of valuable starting material. In this case, it is also convenient and economical to include the isobutylene formed in the product stream in the isobutane recycling stream, since the separation of isobutylene from isobutane would require an extraordinary effort, whereas the separation of a mixture of isobutane and isobutylene from other oxygenate products is reasonably straight forward via conventional separation technologies, since the boiling points of isobutane and isobutylene are close to each other and are much lower than other C2 to C4 oxygenates in the product stream. Through recycling, additional significant amounts of methacrolein and methacrylic acid can be produced from the recycled isobutane and isobutylene, which can greatly enhance the overall yield of methacrolein and methacrylic acid as well as the utilization of isobutane and isobutylene. Thus, this invention provides a process to produce methacrolein and/or methacrylic acid from isobutane and/or isobutylene and a mixture thereof.

Finally, the separation of methacrolein from methacrylic acid, can also be easily achieved with conventional technologies, since the boiling points of these two C4 oxygenates are far apart, at around 69° C. and 163° C., respectively. In addition, methacrolein can be further converted to methacrylic acid using a conventional catalyst suitable for oxidation of an unsaturated aldehyde.

EXAMPLES

The present invention will now be described more specifically with Examples and Comparative Examples, wherein conversion (Conv), selectivity (Sel) and yield (Y) have the following definition:

Conversion(%)=(moles of hydrocarbon consumed/moles of fresh hydrocarbon feed)×100;

Selectivity(%)=(moles of product formed/moles of hydrocarbon consumed)×100;

Yield(%)=(moles of product formed/moles of fresh hydrocarbon feed)×100.

These examples are provided for illustrative purposes only, and are in no way intended to limit the scope of the invention, as set forth in the appended claims.

Example 1

A catalyst with the empirical formula of $Mo_{1.0}Sb_{0.5}Ce_{0.1}$ was prepared as follows. To a flask was added 3.217 g of antimony (III) acetate (Strem Chemical) and 20 g of acetic acid (J. T. Baker), which was then heated to 80° C. until a clear solution was obtained. In separate flasks, 3.800 g of ammonium heptamolybdate tetrahydrate (Strem Chemical) was dissolved in 25 g of water, and 1.180 g of ammonium cerium (IV) nitrate (Strem Chemical) in 20 g of water. The antimony solution was added to the molybdenum solution with vigorous stirring followed by the addition of the cerium solution to form a slurry. The water and acetic acid of the resulting slurry was removed via rotary evaporation to obtain a precursor solid which was further oven dried at 80° C. for 16 h. Six grams of the dried precursor solid was placed in a covered crucible for calcination under an inert (N2 or Ar, Ar preferred) atmosphere. The furnace was heated from room temperature to 350° C. at the rate of about 10° C./min. and held at 350° C. for two hours. Then the temperature was ramped to 650° C. at the rate of about 10° C./min and held at 650° C. for 2 hours. After the calcination, the metal oxide catalyst thus obtained (about 5 g) was then ground to a fine powder and pressed in a mold and then broken and sieved to 12-20 mesh granules. About 1.5 g of the granules were packed in a quartz tubular reactor of 4 mm ID for the evaluation of catalytic performance. The catalytic testing was conducted at 500° C. in a temperature programmable tube furnace. At slightly above atmospheric pressure, the feed-gas mixture of isobutane/air/nitrogen and water-vapor (or steam) with the volume ratio of 1/10/10/0.7 passed through the catalyst bed at a space velocity of about 2,700 $hr^{-1}$. The reaction effluent was analyzed directly using gas chromatography ("GC") to determine the isobutane conversion and the yield and selectivity of the oxidation products. The results are shown in Table 1.

Example 2

A catalyst with the empirical formula of $Mo_{1.0}Sb_{0.5}Bi_{0.1}Sn_{0.01}$ was prepared in the same manner as described in Example-1, except the ammonium cerium (IV) nitrate was replaced with 1.044 g of bismuth (III) nitrate (Aldrich Chemical) dissolving in about 5 g of dilute nitric acid (13%) aqueous solution and in addition, 0.041 g of tin (II) chloride (Aldrich Chemical) in 30 g of water acidified with a few drops of dilute nitric acid (13%) was also added to the slurry mixture. The catalytic testing was also conducted in the same manner as described in Example 1 and results also listed in Table 1.

Example 3

A catalyst with the empirical formula of $Mo_{1.0}Sb_{0.5}Ce_{0.09}Ag_{0.003}$ was prepared in the same manner as described in Example 1, except 30 g of aqueous solution containing 0.011 g of silver nitrate (Aldrich Chemical) was also added to the slurry mixture. The catalytic testing was also conducted in the same manner as described in Example 1 except the feed-gas mixture of isobutane/air/nitrogen and water-vapor (or steam) had volume ratios of 1/5/10/0.5 and flowed at a space velocity of about 2,000 $hr^{-1}$. The testing results are shown in Table 1.

Example 4

A catalyst with empirical formula $Mo_{1.0}Sb_{0.5}Ce_{0.09}Sn_{0.005}Ag_{0.001}$ was prepared in the same manner as described in Example-3, except that there was also added to the slurry mixture an aqueous solution containing the proper amount of tin (II) chloride (Aldrich Chemical) according to the empirical formula, which was prepared in the same manner as described in Example 2. The catalytic testing was conducted in the same manner as described in Example 1, except the feed-gas mixture of isobutane/air/nitrogen and water-vapor (or steam) had volume ratios of 1/43/0/1.3 and testing was conducted at 525° C. The testing results are set forth in Table 1.

TABLE 1

| | Catalyst Composition | feed ratio iBA/air/N$_2$/H$_2$O | Temp ° C. | C4 Conv. (%) | iBE | MAC | MAA | C4 Products |
|---|---|---|---|---|---|---|---|---|
| Ex-1 | $Mo_{1.0}Sb_{0.5}Ce_{0.1}O_n$ | 1/10/10/0.7 | 500 | 26 | 0.9/4 | 8.9/34 | 0.3/1 | 9.8/38 |
| EX-2 | $Mo_{1.0}Sb_{0.5}Bi_{0.1}Sn_{0.01}O_n$ | 1/10/10/0.7 | 500 | 34 | 5.1/15 | 8.2/24 | 0.3/1 | 13.3/39 |
| Ex-3 | $Mo_{1.0}Sb_{0.5}Ce_{0.09}Ag_{0.003}O_n$ | 1/5/10/0.5 | 500 | 21 | 1.2/6 | 9.8/48 | 0.5/2 | 11.5/56 |
| Ex-4 | $Mo_{1.0}Sb_{0.5}Ce_{0.09}Sn_{0.005}Ag_{0.001}O_n$ | 1/43/0/1.3 | 525 | 22 | 4.2/19 | 11.5/52 | 0.3/1 | 15.7/71 | iBA = isobutane,
iBE = isobutylene,
MAC = methacrolein;
MAA = methacrylic acid,
C4 Products = (iBE + MAC + MAA).

Example 5

The catalyst prepared according to Example 4 was subjected to catalytic testing in the same manner as described in Example 1, except the feed-gas mixture was isobutylene/air/nitrogen and water-vapor (or steam) with volume ratios of 1/43/0/1.3. The test results are set forth in Table 2.

Example 6

The catalyst prepared according to Example 4 was subjected to catalytic testing in the same manner as described in Example 5, except the feed-gas mixture had volume ratios of 1/20/0/6.8. The test results are presented in Table 2.

TABLE 2

| Catalyst Composition | C4 feed ratio iBE/air/N$_2$/H$_2$O | Temp °C. | C4 Conv. (%) | Product Yield/Selectivity (%) | | | |
|---|---|---|---|---|---|---|---|
| | | | | AcOH | MAC | MAA | C4 oxygenates |
| Ex-5 Mo$_{1.0}$Sb$_{0.5}$Ce$_{0.09}$Sn$_{0.005}$Ag$_{0.001}$O$_n$ | 1/43/0/1.3 | 500 | 80 | 0.5/1 | 56.4/70 | 1.5/2 | 57.9/72 |
| Ex-6 Mo$_{1.0}$Sb$_{0.5}$Ce$_{0.09}$Sn$_{0.005}$Ag$_{0.001}$O$_n$ | 1/20/0/6.8 | 500 | 86 | 10.3/12 | 39.5/46 | 14.6/17 | 54.1/63 | iBE = isobutylene,
AcOH = acetic acid;
MAC = methacrolein;
MAA = methacrylic acid;
C4 Oxygenates = (MAC + MAA)

Example 7

The catalyst prepared according to Example 4 could be subjected to the oxidation reaction according to Example 4 and Example 5, however, unreacted isobutane and product isobutylene are separated and recycled via conventional methods from the reaction effluent and mixed with the fresh isobutane as the hydrocarbon of the feed stream. With the (iBA+iBE)/air/N$_2$/H$_2$O feed ratio maintained at 1/43/0/1.3, at equilibrium, 0.21 volume of fresh isobutane is fed and consumed continuously, of which 0.137 volume is converted to methacrolein and 0.003 volume to methacrylic acid. With respect to the fresh-fed and consumed isobutane, the yield of methacrolein is 69% and yield of methacrylic acid is 1.5%. The anticipated results, as calculated on the basis of data obtained in Example 4 and 5, are set forth in Table 3.

Example 8

The catalyst prepared according to Example-4 could be subjected to the oxidation reaction according to Example-4 and Example 6, however, unreacted isobutane and product isobutylene are separated and recycled via conventional methods from the reaction effluent and mixed with the fresh isobutane as the hydrocarbon of the feed stream. With the (iBA+iBE)/air/N$_2$/H$_2$O feed ratio maintained at 1/20/0/6.8, at equilibrium, 0.21 volume of fresh isobutane is fed and consumed continuously, of which 0.127 volume is converted to methacrolein and 0.0084 volume to methacrylic acid. With respect to the fresh-fed and consumed isobutane, the yield of methacrolein is 62% and yield of methacrylic acid is 4.8%. The anticipated results, as calculated on the basis of data obtained in Example 4 and 6, are set forth in Table 3.

metavanadate (Aldrich Chemical) and ammonium niobium oxalate (CBMM Chemical Company), respectively. The catalytic testing was conducted in the same manner as described in Example 1 except the testing was conducted at 430° C. and the feed gas mixture of isobutane/air/nitrogen and water-vapor (or steam) had volume ratios of 1/10/10/5.7 and space velocity of about 3,200 hr-1. The test results are similar to those disclosed in JP 09-278680 and are reported in Table 4.

Comparative Example 2

A catalyst with empirical formula Mo$_{1.0}$V$_{0.3}$Te$_{0.16}$Nb$_{0.1}$ was prepared according to the disclosure in JP 09-278680 and JP 10-128112. The sources of Mo, V and Nb are as described in Comparative Example 1 and the source of Te is telluric acid (Aldrich Chemical). The catalytic testing was conducted in the same manner as described in Comparative Example 1. The test results are similar to those disclosed in JP 09-278680 and are reported in Table 4.

Comparative Example 3

A catalyst with empirical formula Mo$_{1.0}$V$_{0.3}$Te$_{0.16}$Nb$_{0.2}$ was prepared as described in Comparative Example 2. The catalytic testing was conducted in the same manner as described in Comparative Example 1, except the testing was carried out at 390° C. The test results are reported in Table 4.

Comparative Example 4

A catalyst with empirical formula Mo$_{1.0}$V$_{0.3}$Nb$_{0.1}$ was prepared as described in Comparative Example 2, except this

TABLE 3

| Catalyst Composition | feed ratio C4/air/N$_2$/H$_2$O (volume) | Fresh IBA fed (volume) | Temp °C. | iBA Conv. (%) | Product Yield or Selectivity (%) | | |
|---|---|---|---|---|---|---|---|
| | | | | | MAC | MAA | C4 Oxygenates |
| Ex-7 Mo$_{1.0}$Sb$_{0.5}$Ce$_{0.09}$Sn$_{0.005}$Ag$_{0.001}$O$_n$ | 1/43/0/1.3 | 0.21 | 500 | 100 | 69 | 1.5 | 70.5 |
| Ex-8 Mo$_{1.0}$Sb$_{0.5}$Ce$_{0.09}$Sn$_{0.005}$Ag$_{0.001}$O$_n$ | 1/20/0/6.8 | 0.21 | 500 | 100 | 62 | 4.8 | 66.8 |

Unreacted iBA and product iBE recycled and 100% of fresh-fed isobutane consumed; iBA = isobutane, iBE = isobutylene, C4 = (iBA + iBE); MAC = methacrolein; MAA = methacrylic acid; C4 Oxygenates = (MAC + MAA)

Comparative Example 1

A catalyst with empirical formula Mo$_{1.0}$V$_{0.3}$Sb$_{0.7}$Nb$_{0.1}$ was prepared according to the disclosure in JP 09-278680 and JP 10-128112. The sources of Mo and Sb are as described in Example 1 and the sources of V and Nb are ammonium catalyst contained no Te. The catalytic testing was conducted in the same manner as described in Comparative Example 1, except the testing was conducted at 350° C. and the feed gas mixture of isobutane/air/nitrogen and water-vapor (or steam) had volume ratios of 1/20/0/5.7. The test results are reported in Table 4.

TABLE 4

| Catalyst Composition | feed ratio iBA/air/N$_2$/H$_2$O | Temp °C. | IBA Conv. (%) | Yield/Selectivity (%) | | | |
|---|---|---|---|---|---|---|---|
| | | | | AcOH | MAC | MAA | C4 Oxygenates |
| CE-1 Mo$_{1.0}$V$_{0.3}$Sb$_{0.7}$Nb$_{0.1}$O$_n$ | 1/10/10/5.7 | 430 | 11 | 0.1/1 | 2.3/21 | 0/0 | 2.3/21 |
| CE-2 Mo$_{1.0}$V$_{0.3}$Te$_{0.16}$Nb$_{0.1}$O$_n$ | 1/10/10/5.7 | 430 | 10 | 0.1/1 | 1.4/13 | 0/0 | 1.4/13 |
| CE-3 Mo$_{1.0}$V$_{0.3}$Te$_{0.16}$Nb$_{0.2}$O$_n$ | 1/10/10/5.7 | 390 | 18 | 1.8/10 | 1.9/10 | 0.4/2 | 2.3/12 |
| CE-4 Mo$_{1.0}$V$_{0.3}$Nb$_{0.1}$O$_n$ | 1/20/0/5.7 | 350 | 34 | 18/54 | 0.2/0.6 | 0/0 | 0.2/0.6 | iBA = isobutane;
AcOH = acetic acid;
MAC = methacrolein;
MAA = methacrylic acid;
C4 Oxygenates = (MAC + MAA)

The entire disclosure of every patent and journal article cited in the foregoing specification is incorporated by reference herein.

While certain embodiments of the present invention have been described and/or exemplified above, various other embodiments will be apparent to those skilled in the art from the foregoing disclosure. The present invention is, therefore, not limited to the particular embodiments described and/or exemplified, but is capable of considerable variation and modification without departure from the scope of the appended claims.

What is claimed is:

1. A process for producing at least one of an unsaturated aldehyde and an unsaturated carboxylic acid, comprising subjecting a feed gas mixture including an alkane, an alkene, or a mixture thereof, and air or oxygen, and, optionally, one or more diluting gases, to a vapor phase oxidation in a heated reactor in the presence of a solid catalyst comprising a compound having the formula $$A_a B_b X_x Y_y Z_z O_o$$

wherein A is at least one of the group of elements Mo, W and Zr, B is at least one of the group of elements Bi, Sb, Se and Te, X is at least one of the group of elements Al, Bi, Ca, Ce, Co, Fe, Ga, Mg, Ni, Sn, W and Zn, Y, if present, is at least one of the group of elements Ag, Au, B, Cr, Cs, Cu, K, La, Li, Mg, Mn, Na, Nb, Ni, P, Pb, Rb, Re, Ru, Sn, Te, Ti, Zr, and Z, if present, is at least one element selected from said X or Y groups or from the following: As, Ba, Pd, Pt, Sr, or mixtures thereof, and wherein a=1, 0.05<b<1.5, 0.01<x<1, 0<y<0.5, 0<z<0.2 and o is dependent on the oxidation state of the other elements.

2. The process according to claim 1 wherein said feed gas mixture is an alkane and air or oxygen, and, optionally, one or more diluting gases, and the resulting product is at least one or more of an, an unsaturated aldehyde and an unsaturated carboxylic acid of the same or less carbon number.

3. The process according to claim 1 wherein said reactor is a tubular or a fluidize-bed reactor maintained at a temperature range of 200-600° C. and the contact time of said feed gas mixture with said catalyst is within a range of 0.1-10 seconds.

4. The process according to claim 1 wherein said at least one alkane and alkene have carbon number between 2 to 6.

5. The process according to claim 1 wherein said feed gas mixture includes isobutane or isobutylene, or a mixture thereof and the resulting unsaturated aldehyde is 2-methyl-2-propen-1-al(methacrolein) and the unsaturated acid is methacrylic acid.

6. The process according to claim 1 wherein said feed gas is isobutane and air or oxygen, and, optionally, one or more diluting gases, and the resulting products is at least one of isobutylene, methacrolein and methacrylic acid.

7. The process according to claim 1, wherein the feed gas mixture contains steam and/or nitrogen as diluting gases, thereby favoring the production of unsaturated aldehyde and/or unsaturated carboxylic acid.

8. The process according to claim 1 wherein any alkane, alkene or mixture thereof present in the product stream is separated and recycled to form part of the feed gas mixture.

9. The process according to claim 1, wherein A is Mo or W or a mixture thereof, B is at least one of the group of elements Bi and Sb, X is at least one of the group of elements Bi, Ca, Ce, Co, Ga, Mg, Ni, Sn, and Zn, Y, if present, is at least one of the group of elements Ag, Au, La, Mn, P, Pb, Sn, Te, or Zr, and Z, if present, is at least one of the elements from the X group, Y group or Al, B, Ba, K, Na, Pd, Sr.

10. The process according to claim 1, wherein A is Mo, B is Sb, X is at least one of the group of elements Bi and Ce, Y, if present, is at least one of the group of elements Ag, Au and Sn, and Z, if present, is at least one element from the X group, Y group or Al, B, Ba, K, Na, Pd, Sr.

11. The process according to claim 1, wherein a=1, 0.05<b<1, 0.01<x<0.3, 0<y<0.1, 0<z<0.05 and o is dependent on the oxidation state of the other elements.

12. The process according to claim 1, wherein said catalyst is dispersed onto and/or into a high surface area support material.

13. A solid catalyst comprising a compound having the formula $$A_a B_b X_x Y_y Z_z O_o$$

wherein A is at least one of the group of elements Mo, W and Zr, B is at least one of the group of elements Bi, Sb, Se and Te, X is at least one of the group of elements Al, Bi, Ca, Ce, Co, Fe, Ga, Mg, Ni, Sn, W and Zn, and Y, if present, is at least one of the group of elements Ag, Au, B, Cr, Cs, Cu, K, La, Li, Mg, Mn, Na, Nb, Ni, P, Pb, Rb, Re, Ru, Sn, Te, Ti, and Zr, and Z, if present, is at least one element from said X or Y groups or from the following: As, Ba, Pd, Pt, Sr, or mixtures thereof, and wherein a=1, 0.05<b<1.5, 0.01<x<1, 0<y<0.5, 0<z<0.2 and o is dependent on the oxidation state of the other elements.

14. The catalyst according to claim 13, wherein A is Mo or W or a mixture thereof, B is at least one of the group of elements Bi and Sb, X is at least one of the group of elements Bi, Ca, Ce, Co, Ga, Mg, Ni, Sn, and Zn, Y, if present, is at least one of the group of elements Ag, Au, La, Mn, P, Pb, Sn, Te, and Zr, and Z, if present, is at least one of the elements from the X group, Y group or Al, B, Ba, K, Na, Pd and Sr.

15. The catalyst according to claim 13, wherein a=1, 0.05<b<1, 0.01<x<0.3, 0<y<0.1, 0<z<0.05 and o is dependent on the oxidation state of the other elements.

16. The catalyst according to claim 13, which is dispersed onto and/or into a high surface area support material.

17. The catalyst according to claim 16, wherein the support material has high surface-area and comprises oxides, carbides, or nitrides of at least one element from the group of Al, Mg, Si, Ti, and Zr, and Zr or composites thereof.

18. The catalyst according to claim 16, wherein the support material comprises alumina, silica, silicon carbide, silicon nitrile, titania, zeolites, zirconia, or a composite thereof.

19. A process for preparing a solid catalyst comprising a compound having the formula $$A_aB_bX_xY_yZ_zO_o$$

wherein A is at least one of the group of elements Mo, W and Zr, B is at least one of the group of elements Bi, Sb, Se and Te, X is at least one of the group of elements Al, Bi, Ca, Ce, Co, Fe, Ga, Mg, Ni, Sn, W and Zn, Y, if present, is one or more elements selected from the group of Ag, Au, B, Cr, Cs, Cu, K, La, Li, Mg, Mn, Na, Nb, Ni, P, Pb, Rb, Re, Ru, Sn, Te, Ti, Zr, and Z, if present, is at least one element selected from said X or Y groups or from the following: As, Ba, Pd, Pt, Sr, or mixtures thereof, and wherein a=1, 0.05<b<1.5, 0.01<x<1, 0<y<0.5, 0<z<0.2 and o is dependent on the oxidation state of the other elements, said process comprising:
   a) forming a mixture by dry-mixing of the appropriate amounts of source materials containing selected ones of said elements to provide said elements in predetermined a, b, x, y and z ratios; and
   b) calcining said mixture at a temperature from 150° C. to 900° C. under an atmosphere containing oxygen or an inert gas or a mixture thereof, to yield said solid catalyst.

20. A process for preparing a solid catalyst comprising a compound having the formula $$A_aB_bX_xY_yZ_zO_o$$

wherein A is at least one of the group of elements Mo, W and Zr, B is at least one of the group of elements Bi, Sb, Se and Te, X is at least one of the group of elements Al, Bi, Ca, Ce, Co, Fe, Ga, Mg, Ni, Sn, W and Zn, Y, if present, is one or more elements selected from the group of Ag, Au, B, Cr, Cs, Cu, K, La, Li, Mg, Mn, Na, Nb, Ni, P, Pb, Rb, Re, Ru, Sn, Te, Ti, Zr, and Z, if present, is at least one element selected from said X or Y groups or from the following: As, Ba, Pd, Pt, Sr, or mixtures thereof, and wherein a=1, 0.05<b<1.5, 0.01<x<1, 0<y<0.5, 0<z<0.2 and o is dependent on the oxidation state of the other elements, said process comprising:
   a) forming a mixture of the appropriate amounts of source materials containing selected ones of said elements to provide said elements in predetermined a, b, x, y and z ratios, and at least one liquid substance to form a solution or slurry containing the said source materials;
   b) removing part or all of the said liquid substance(s) from said mixture to obtain a solid catalyst precursor; and
   c) calcining said catalyst precursor at a temperature from 150° C. to 900° C. under an atmosphere containing oxygen or an inert gas or a mixture thereof, to yield said solid catalyst.

21. The process according to claim 19 or 20, wherein the catalyst precursor may undergo calcinations at multiple stages with at least one low-temperature stage at temperature from 150° C. to 350° C., and at least one high-temperature stage at temperature from 350° C. to 900° C.

22. The process according to claim 21, wherein the temperature for a said high-temperature stage is from 450° C. to 700° C.

23. The process according to claim 19 or 20, wherein inert gas is used in said calcinations and comprises at least one of argon and nitrogen.

24. The process according to claim 23, wherein said inert gas is argon.

25. The process according to claim 19 or 20, wherein said liquid substance(s) is at least one liquid selected from the group consisting of water, alcohols, ketones, ethers, acids, aliphatic and aromatic compounds.

26. The process according to claim 19 or 20, wherein said catalyst is dispersed onto and/or into a support material having high surface-area.

27. The process according to claim 26, wherein said catalyst support material has high surface-area and comprises oxides, carbides, or nitriles of at least one element from the group of Al, Mg, Si, Ti, and Zr or composites thereof.

28. The process according to claim 27, wherein said catalyst support material comprises alumina, carbon, niobia, silica, silicon carbide, silicon nitride, titania, zeolite, zirconia, or a composite thereof.

29. The process according to claim 26, wherein the elements of the said catalyst are dispersed onto and/or into said support material by a procedure selected from the group of wetting, impregnation, sol-gel, co-gel, precipitating, co-precipitating, ion-exchange, vapor depositing, reversed microemulsion depositing and a combination thereof.

30. A solid catalyst comprising a compound having the formula $$A_aB_bX_xY_yZ_zO_o$$

wherein A is Mo, B is Sb, X is at least one of the group of elements Bi and Ce, Y, if present, is at least one of the group of elements Ag, Au, and Sn, and Z, if present, is at least one element from the X group, Y group or Al, B, Ba, K, Na, Pd and Sr, wherein a=1, 0.05<b<1.5, 0.01<x<1, 0<y<0.5, 0<z<0.2 and o is dependent on the oxidation state of the other elements.

31. A process for producing at least one of an unsaturated aldehyde and an unsaturated carboxylic acid, comprising subjecting a feed gas mixture including an alkane, an alkene, or a mixture thereof, and air or oxygen, and, optionally, one or more diluting gases, to a vapor phase oxidation in a heated reactor in the presence of a solid catalyst as claimed in claim 30.

32. The process according to claim 31 wherein said feed gas mixture includes isobutane or isobutylene, or a mixture thereof and the resulting unsaturated aldehyde is 2-methyl-2-propen-1-al (methacrolein) and the unsaturated acid is methacrylic acid.

33. The process according to claim 31 wherein said feed gas is isobutane and air or oxygen, and, optionally, one or more diluting gases, and the resulting products is at least one of isobutylene, methacrolein and methacrylic acid.

* * * * *